(12) United States Patent
Dan et al.

(10) Patent No.: US 11,064,721 B2
(45) Date of Patent: Jul. 20, 2021

(54) METHOD FOR PRODUCING IMMUNE ACTIVATOR AND METHOD FOR PRODUCING FOOD AND DRINK FOR IMMUNE ACTIVATION

(71) Applicants: Kazuhito Torii, Tokyo (JP); Tomoko Torii, Tokyo (JP)

(72) Inventors: Katsuaki Dan, Tokyo (JP); Kazuhito Torii, Tokyo (JP)

(73) Assignees: Kazuhito Tore, Tokyo (JP); Tomoko Torii, Tokyo (JP)

( * ) Notice: Subject to any disclaimer, the term of this patent is extended or adjusted under 35 U.S.C. 154(b) by 0 days.

(21) Appl. No.: 16/480,917

(22) PCT Filed: Oct. 10, 2018

(86) PCT No.: PCT/JP2018/037643
§ 371 (c)(1),
(2) Date: Jul. 25, 2019

(87) PCT Pub. No.: WO2019/106967
PCT Pub. Date: Jun. 6, 2019

(65) Prior Publication Data
US 2019/0387780 A1 Dec. 26, 2019

(30) Foreign Application Priority Data
Nov. 30, 2017 (JP) .............................. JP2017-230085

(51) Int. Cl.
| A61K 36/28 | (2006.01) |
| A23L 33/105 | (2016.01) |
| A23L 2/52 | (2006.01) |
| A61K 36/63 | (2006.01) |
| A61K 36/78 | (2006.01) |

(52) U.S. Cl.
CPC ............... *A23L 33/105* (2016.08); *A23L 2/52* (2013.01); *A61K 36/28* (2013.01); *A61K 36/63* (2013.01); *A61K 36/78* (2013.01)

(58) Field of Classification Search
None
See application file for complete search history.

(56) References Cited

U.S. PATENT DOCUMENTS

2007/0082068 A1   4/2007 Satsu et al.

FOREIGN PATENT DOCUMENTS

| CN | 104171188 A |   | 12/2014 |
| CN | 105124080   | * | 12/2015 |
| CN | 105124080 A | * | 12/2015 |
| CN | 105831355   | * | 8/2016  |
| JP | H06-22693 A |   | 2/1994  |
| JP | 2004-254685 A |  | 9/2004 |
| JP | 2005/245346 | * | 9/2005 |
| JP | 2005-245346 A |  | 9/2005 |
| JP | 2007-89554 A |  | 4/2007 |
| JP | 2010-235544 A | | 10/2010 |
| JP | 2016-160238 A | | 9/2016 |
| KR | 1551377 B1 | * | 9/2015 |
| WO | 2005/051405 A1 | | 6/2005 |
| WO | WO 2005/051405 | * | 6/2005 |

OTHER PUBLICATIONS

Nov. 6, 2018 Search Report issued in International Patent Application No. PCT/JP2018/037643.
Jan. 6, 2020 Office Action issued in Taiwanese Patent Application No. 108108261.
Apr. 29, 2020 Office Action issued in Taiwanese Patent Application No. 108108261.
May 19, 2020 Office Action issued in Japanese Patent Application No. 2017-230085.
Jun. 2, 2020 International Preliminary Report on Patentability issued in PCT Application No. PCT/JP2018/037643.

* cited by examiner

*Primary Examiner* — Ralph J Gitomer
(74) *Attorney, Agent, or Firm* — Oliff PLC

(57) ABSTRACT

A drying step of drying *Gynura procumbens* at 0° C. or more and 40° C. or less; and a cutting/pulverizing step of cutting or pulverizing the *Gynura procumbens* dried in the drying step while keeping at 0° C. or more and 40° C. or less are included.

6 Claims, 7 Drawing Sheets

METHOD FOR PRODUCING IMMUNE ACTIVATOR AND METHOD FOR PRODUCING FOOD AND DRINK FOR IMMUNE ACTIVATION

TECHNICAL FIELD

The present invention relates to a method for producing an immune activator and a method for producing food and drink for immune activation.

BACKGROUND ART

Immunity is a defense system to defend against adverse effects of invasion of antigens such as bacteria and viruses into the body. Immunity in the living body can be roughly divided into two, innate immunity and acquired immunity.

The innate immunity acts as soon as antigen enters the body and transmits information on the antigen to the acquired immunity. Here, macrophages, natural killer cells, dendritic cells and the like are involved in the innate immunity, and elimination by digestion and degradation of antigens, production of cytokines and the like are carried out.

In addition, the acquired immunity is carried out by T cells to which information was transmitted by immune cells involved in the innate immunity of macrophages or the like. Here, the T cells involved in the acquired immunity are transformed into Th1 cells or Th2 cells by immature helper T cells receiving differentiation induction stimulation by cytokines or the like. The Th1 cells are involved in cell-mediated immunity and enhance biological defense abilities such as infection prevention and anti-tumor immunity. Also, the Th2 cells are involved in humoral immunity.

In addition, various researches have been conducted on an immune activator for enhancing biological defense abilities such as infection prevention and anti-tumor immunity and treating or preventing infectious diseases and cancer (see, for example, Patent Literature 1 and Patent Literature 2).

In Patent Literature 1, studies are conducted on plants of the genus *Salacia* or extracts thereof, and metabolites of tea-derived catechins in Patent Literature 2, respectively.

In addition, as described in Patent Literature 2 that "the action of catechin metabolites on NK cell (natural killer cell) activity is unknown", it is considered that there are many unknown actions of components derived from natural products.

CITATION LIST

Patent Literature

Patent Literature 1: JP 2010-235544 A
Patent Literature 2: JP 2016-160238 A

SUMMARY OF INVENTION

Technical Problem

An object of the present invention is to provide a method for producing a novel immune activator derived from a natural product and a method for producing food and drink for immune activation.

Solution to Problem

As a result of intensive studies, the present inventors have found that the above object can be achieved by using *Gynura* (the genus *Gynura* of the family Asteraceae), thereby completing the present invention.

That is, according to the present invention, there are provided (1) a method for producing an immune activator including: a drying step of drying *Gynura procumbens* at 0° C. or more and 40° C. or less; and a cutting/pulverizing step of cutting or pulverizing the *Gynura procumbens* dried in the drying step while keeping at 0° C. or more and 40° C. or less, (2) the method for producing an immune activator according to (1), wherein at least one of leaves or stems of *Gynura procumbens* is used as the *Gynura procumbens*, (3) the method for producing an immune activator according to (1) or (2), further including a step of adding at least one of vitamins, olive or an extract of olive, and *Houttuynia cordata* or an extract of *Houttuynia cordata*, and (4) a method for producing food and drink for immune activation, including a step of blending the immune activator obtained by the method for producing an immune activator according to any one of (1) to (3) in a food or drink.

Advantageous Effects of Invention

According to the present invention, a method for producing a novel immune activator derived from a natural product and a method for producing food and drink for immune activation are provided.

DESCRIPTION OF EMBODIMENTS

Hereinafter, a method for producing an immune activator of the present invention and a method for producing food and drink for immune activation will be described. A method for producing an immune activator of the present invention includes a drying step of drying *Gynura* at 0° C. or more and 40° C. or less and a cutting/pulverizing step of cutting or pulverizing the *Gynura* dried in the drying step while keeping at 0° C. or more and 40° C. or less.

The *Gynura* belongs to the genus *Gynura* of the family Asteraceae. Examples of the genus *Gynura* include *Gynura bicolor, Gynura cusimbua, Gynura divaricata, Gynura eliptica, Gynura formosana, Gynura japonica* (*Gynura segetum*), *Gynura nepalensis, Gynura procumbens, Gynura pseudochina* and the like, and *Gynura procumbens* can be suitably used.

As *Gynura procumbens*, any one of leaves, stems, roots and the like may be used, but leaves or stems are preferably used, and leaves are more preferably used.

As *Gynura procumbens*, any one of leaves, stems, roots and the like may be used, but leaves or stems are preferably used, and leaves are more preferably used.

It is preferable to use *Gynura* which has been dried after collection, and cut or pulverized. Drying is preferably carried out at a temperature condition of 0° C. or more and 40° C. or less, preferably 0° C. or more and 36° C. or less, and more preferably 0° C. or more and 34° C. or less. Also, it is preferable to carry out low temperature dehumidification drying.

When drying is carried out at a temperature higher than the above temperature, it is considered that a component exhibiting the effect of the present invention among components contained in *Gynura* is modified or decomposed, and the effect of the present invention cannot be obtained. Also, even when frozen and stored before or after cutting or pulverization, the effect of the present invention cannot be obtained.

Moreover, the humidity at the time of low temperature dehumidification drying is preferably 10% or less in relative humidity. In addition, the low temperature dehumidification drying is preferably carried out for several hours to 50 hours, and more preferably carried out for 10 hours to 30 hours.

Further, the method for cutting or pulverizing *Gynura* can be performed by a known cutting or pulverizing method, but it is preferable to cut or pulverize leaves of *Gynura* while keeping at the temperature range under the above drying conditions. In order to perform such a method, it is preferable to use a cooling type pulverizer, and for example, a bead mill or homogenizer which performs pulverization while cooling, a water cooling type stone mill or the like can be used.

From the viewpoint of keeping the preservation state of *Gynura* good, it is not preferable to juice *Gynura* with a juicer or the like and store it in a state containing moisture. It is preferable to store *Gynura* in a dried state as in the present invention.

The *Gynura* treated as described above can be used as an immune activator.

Olive or an extract of olive, or *Houttuynia cordata* or an extract of *Houttuynia cordata* may be added to the *Gynura* treated as described above. In addition, additional components such as vitamins, amino acids, proteins, minerals, fatty acids and peptides may be added to the immune activator containing *Gynura* or an extract of *Gynura* of the present invention. Vitamins are preferably added as additional components, and examples of the vitamins include vitamin A, vitamin B, vitamin C, vitamin E or derivatives of these vitamins.

The weight ratio of the *Gynura* treated as described above to the total amount of olive or an extract of olive, or *Houttuynia cordata* or an extract of *Houttuynia cordata* and additional components is preferably 50:50 to 100:0, more preferably 70:30 to 100:0, and further preferably from 80:20 to 100:0.

The immune activator obtained by the method for producing an immune activator of the present invention can be blended in foods, drinks, and the like. Examples of the foods include breads, noodles, confectioneries, meat processed products, fish processed products, frozen foods, jellies, ice creams, dairy products, various seasonings, and the like. In addition to general foods, it can be blended in foods for specified health use, quasi-drugs, health foods, and supplements. Examples of the drinks include soft drinks, milk drinks, alcoholic beverages, tea, black tea drinks, coffee, fruit juice drinks, carbonated drinks, mineral water, fruit and vegetable drinks, and the like.

In addition, a food or drink blended with the immune activator obtained by the method for producing an immune activator of the present invention may be in the same form as an oral administration preparation such as a tablet, capsule, or syrup.

Also, when producing a food or drink blended with the immune activator obtained by the method for producing an immune activator of the present invention, if necessary, additives such as sweeteners, colorants, preservatives, thickeners, stabilizers, gelling agents, antioxidants, coloring agents, bleaching agents, emulsifiers, swelling agents, acidulants, brighteners and fragrances; solvents; and oils may be added. One of these additives may be used alone, or two or more of these additives may be used in combination.

The proportion of the immune activator blended in the food or drink can be appropriately adjusted according to the purpose of use, but the proportion of the immune activator blended in the food or drink is preferably 0.0001 to 80% by weight, more preferably 0.003 to 50% by weight, and further preferably 0.005 to 30% by weight.

In addition, the immune activator obtained by the production method of the present invention is useful in the field of medicine for applications for treating or preventing infectious diseases and cancer. The immune activator of the present invention may be used singly or may be mixed with a generally pharmaceutically acceptable additive and formulated. In addition, examples of an administration form include administration forms using an oral agent such as a tablet, a granule, a capsule, a pill, a powder, a liquid, a suspension, an emulsion, a syrup, an elixir or an extract, administration forms using a parenteral agent such as an injection, a solution, a suppository, an ointment, a patch, a cataplasm or a lotion, and the like, but it is not particularly limited and can be appropriately selected according to the purpose of the treatment and the like.

In the case of a tablet, a granule, a pill, a capsule or a powder, additives such as excipients, binders, disintegrants, and lubricants can be contained. Examples of the excipients include starch, carboxymethyl cellulose, white sugar, dextrin, corn starch, and the like.

Examples of the binders include crystalline cellulose, crystalline cellulose carmellose sodium, methyl cellulose, hydroxypropyl cellulose, low-substituted hydroxypropyl cellulose, hydroxypropyl methyl cellulose, hydroxypropyl methyl cellulose phthalate, hydroxypropyl methyl cellulose acetate succinate, carmellose sodium, ethyl cellulose, carboxymethyl ethyl cellulose, hydroxyethyl cellulose, wheat starch, rice starch, corn starch, potato starch, dextrin, pregelatinized starch, partially pregelatinized starch, hydroxypropyl starch, pullulan, polyvinyl pyrrolidone, amino alkyl methacrylate copolymer E, amino alkyl methacrylate copolymer RS, methacrylic acid copolymer L, methacrylic acid copolymer, polyvinyl acetal diethylamino acetate, polyvinyl alcohol, gum arabic, powdered acacia, agar, gelatin, white shellac, tragacanth, refined white sugar, and macrogol.

Examples of the disintegrants include crystalline cellulose, methylcellulose, low-substituted hydroxypropyl cellulose, carmellose, carmellose calcium, carmellose sodium, croscarmellose sodium, wheat starch, rice starch, corn starch, potato starch, partially pregelatinized starch, hydroxypropyl starch, carboxymethyl starch sodium, and tragacanth.

Examples of the lubricants include wheat starch, rice starch, corn starch, stearic acid, calcium stearate, magnesium stearate, hydrated silicon dioxide, light anhydrous silicic acid, synthetic aluminum silicate, dried aluminum hydroxide gel, talc, magnesium aluminometasilicate, calcium hydrogen phosphate, anhydrous calcium hydrogen phosphate, sucrose fatty acid ester, waxes, hydrogenated vegetable oil, and polyethylene glycol.

In addition, in the case of a liquid, a syrup, a suspension, an emulsion or an elixir, in addition to commonly used inert diluents such as water and vegetable oils, coloring agents, corrigents, flavoring agents and the like may be contained as additives.

Also, in the case of an injection, additives such as suspensions, emulsions and solubilizing agents in use can be contained. Moreover, in the case of an ointment or a suppository, fats, fat oils, lanolin, vaseline, paraffin, waxes, resins, plastic, bases, glycols, higher alcohols, water, emulsifiers and suspending agent can be contained as additives. Further, in the case of a cataplasm, glycerin, water, water-soluble polymers, water-absorbing polymers and the like can be contained as additives. Furthermore, in the case of a lotion, solvents, emulsifying agents, suspending agents and the like can be contained as additives.

EXAMPLES

Hereinafter, the present invention will be described by way of examples, but the present invention is not limited thereto. In these examples, parts and % are by weight unless otherwise specified.

In these examples, for *Gynura*, (1) study of immune induction reaction, (2) study of innate immune response and acquired immune response, and (3) study of cytotoxic activity on cancer cells were carried out.

(1) Study of Immune Induction Reaction

Preparation of Specimens

As specimens of leaves of *Gynura* to be used for study of immune induction reaction, four kinds described below were prepared.

Specimen A. The collected leaves of *Gynura* (*Gynura procumbens*) were subjected to low temperature dehumidification drying under conditions of 20 to 30° C. and a relative humidity of 10% or less. The low temperature dehumidified and dried *Gynura* leaves were pulverized at 20 to 30° C. and added to ultrapure water to obtain a specimen.

Specimen B. The collected leaves of *Gynura* (*Gynura procumbens*) were subjected to a low speed juicer at room temperature (about 25° C.), and both the resulting liquid and fiber were used as a specimen.

Specimen C. The collected leaves of *Gynura* (*Gynura procumbens*) were subjected to a low speed juicer at room temperature (about 25° C.), and only the liquid out of the resulting liquid and fiber was used as a specimen.

Specimen D. The specimen B was frozen and then thawed and used as a specimen.

Also, leaves were used as they were as specimens for leaves of loquat, leaves of Sasa albo-marginata, leaves of *Angelica keiskei* and leaves of *Houttuynia cordata*.

Study of Immune Induction Reaction

The specimens A to D, the specimens of leaves of loquat, leaves of Sasa albo-marginata, leaves of *Angelica keiskei* and leaves of *Houttuynia cordata* were each diluted to 1/10000 and added to mouse spleen cells, and changes in the amount of cytokine-mRNA at that time was studied by quantitative PCR method.

More specifically, cases where the changes in the amount of cytokine-mRNA of six kinds using (i) no immune induction reactant, (ii) 2 μg/mL concanavalin A (ConA) as an immune induction reactant, (iii) 1 μg/mL lipopolysaccharide (LPS) were studied. In addition, cases where these (i) to (iii) were performed without adding the specimen (hereinafter referred to as "only drug stimulation") were also studied.

Figure 1:
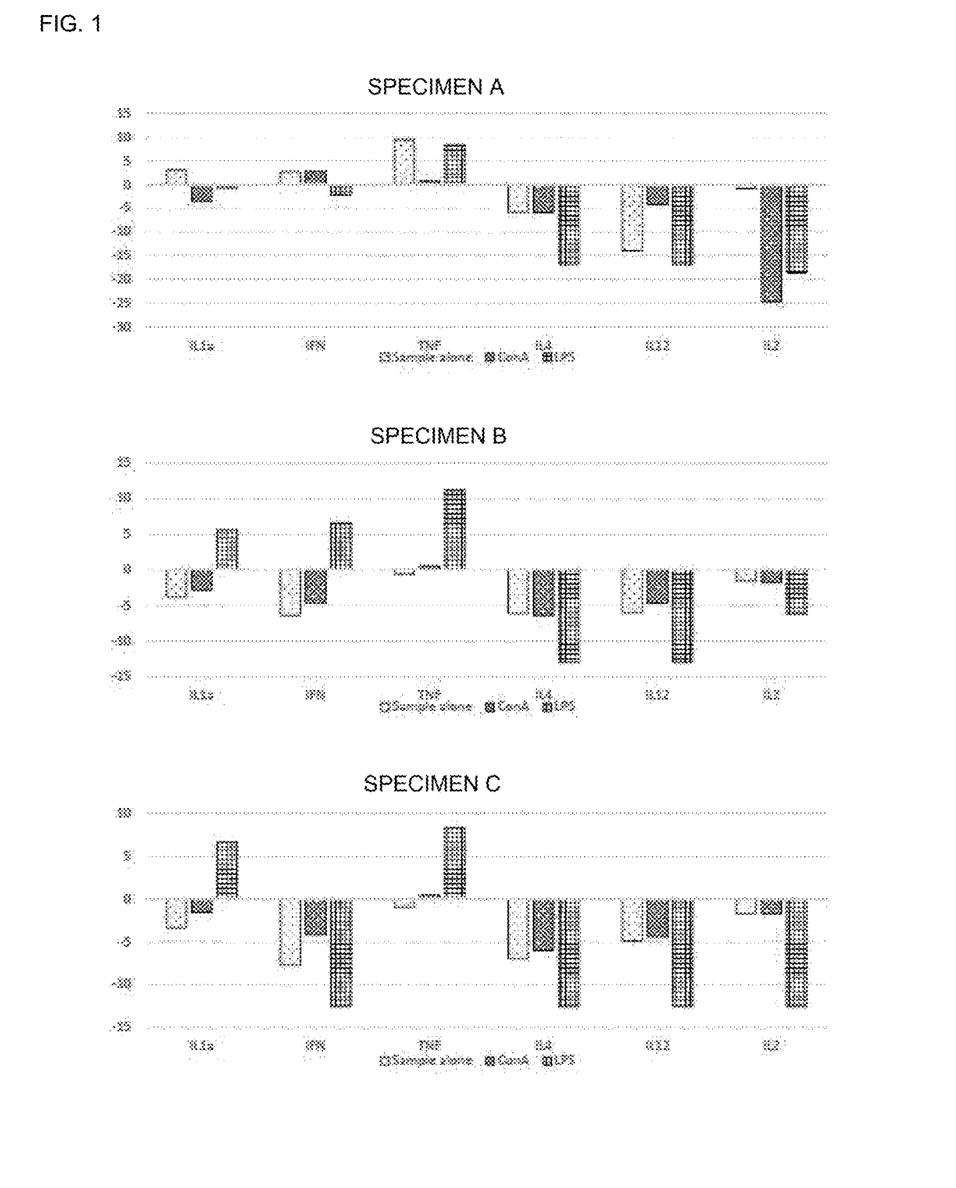
FIG. 1 illustrates graphs of results of a study of immune induction reaction.
Figure 2:
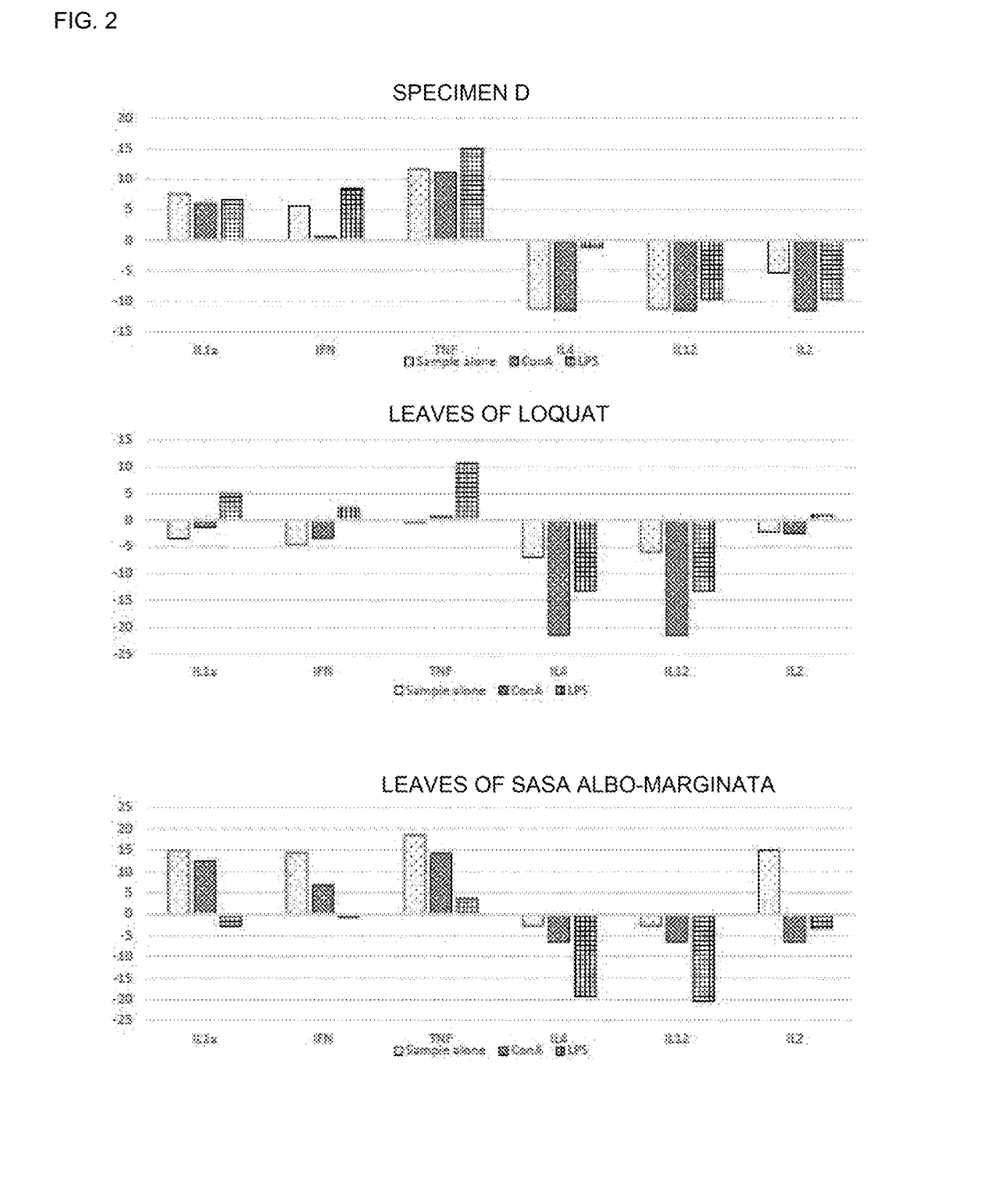
FIG. 2 illustrates graphs of results of the study of immune induction reaction.
Figure 3:
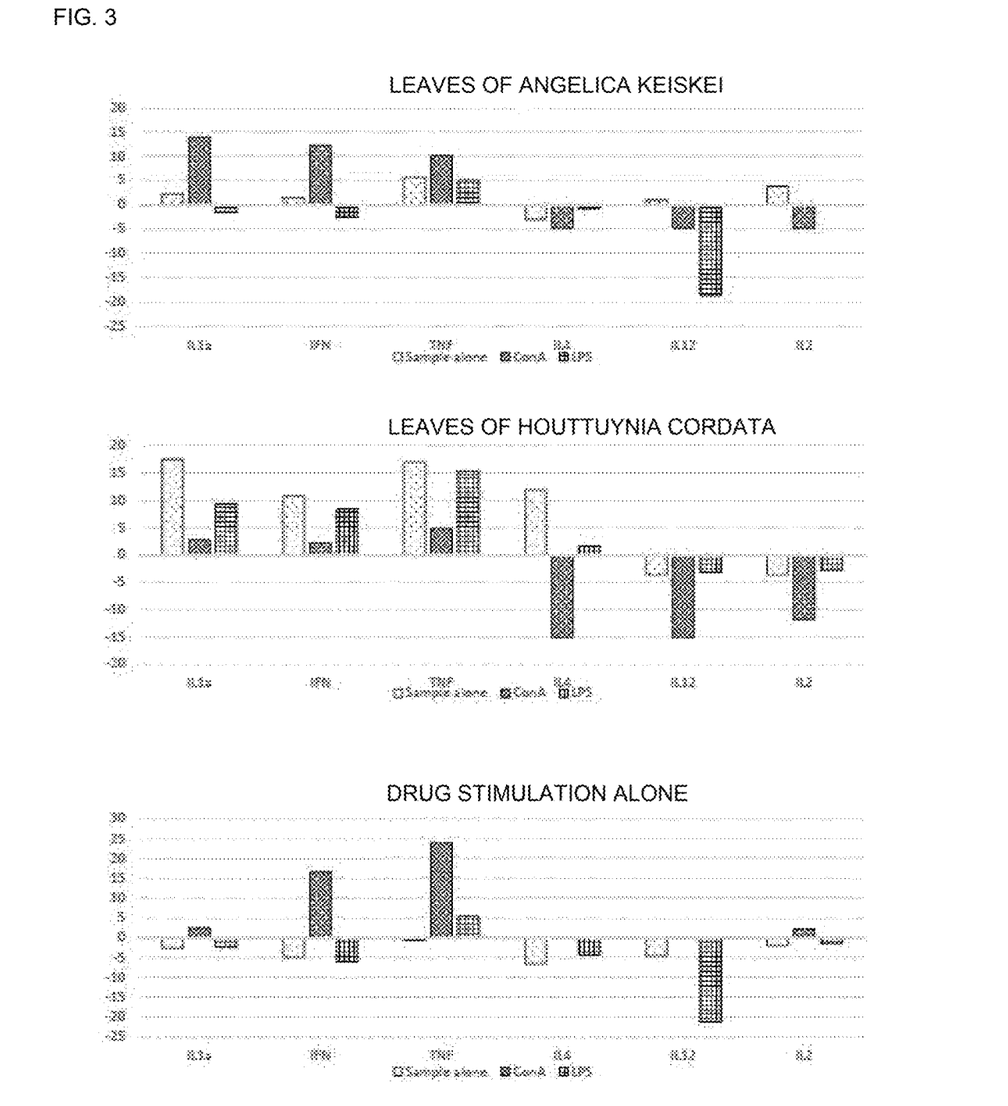
FIG. 3 illustrates graphs of results of the study of immune induction reaction.

In addition, as cytokines, six types, IL1a, IFN, TNF, IL4, IL12 and IL2, were studied. The results are shown in FIGS. 1 to 3. The difference from a relative expression level on the basis of mRNA (GAPDH) constantly expressed in the cells was shown as Delta Ct value (difference in PCR cycle number). The results are shown in FIGS. 1 to 3.

It is considered based on FIGS. 1 to 3 that, from the degree of increase in IL1a, IFN and IL4, in the specimens of leaves of *Gynura* (the specimens A to D), the specimen A pulverized after low temperature dehumidification drying can efficiently extract or hold an active ingredient causing an immune reaction. In addition, from the degree of increase in IL1a, IFN and IL4, it was suggested that the action of the specimens of leaves of Sasa albo-marginata and leaves of *Houttuynia cordata* is strong.

(2) Study of Innate Immune Response and Acquired Immune Response

Preparation of Specimens

The specimen A used for the study of immune induction reaction was used as a specimen of leaves of *Gynura* used for study of innate immune response and acquired immune response (hereinafter referred to as "specimen of leaves of *Gynura*" in this section).

Also, leaves of *Houttuynia cordata* and leaves of olive were used as specimens. A specimen was also prepared for fucoidan so as to have a concentration equivalent to the specimen of leaves of *Gynura*.

Study of Innate Immune Response

Macrophages were isolated from a mouse, and each specimen was diluted to 1/100, 1/1000, 1/10000 and 1/100000, respectively, added thereto, followed by adding a fixed amount of fluorescent beads, and the mixture was cultured for 8 hours. Then, the cultured macrophages were observed with a fluorescence microscope, and the amount of uptaken fluorescent beads was digitized as the amount of fluorescence.

As specimens, specimens of leaves of *Gynura*, leaves of *Houttuynia cordata*, leaves of olive and fucoidan, and a mixed specimen of the four kinds were used. Also, Control using none of these specimens was studied.

Figure 4:
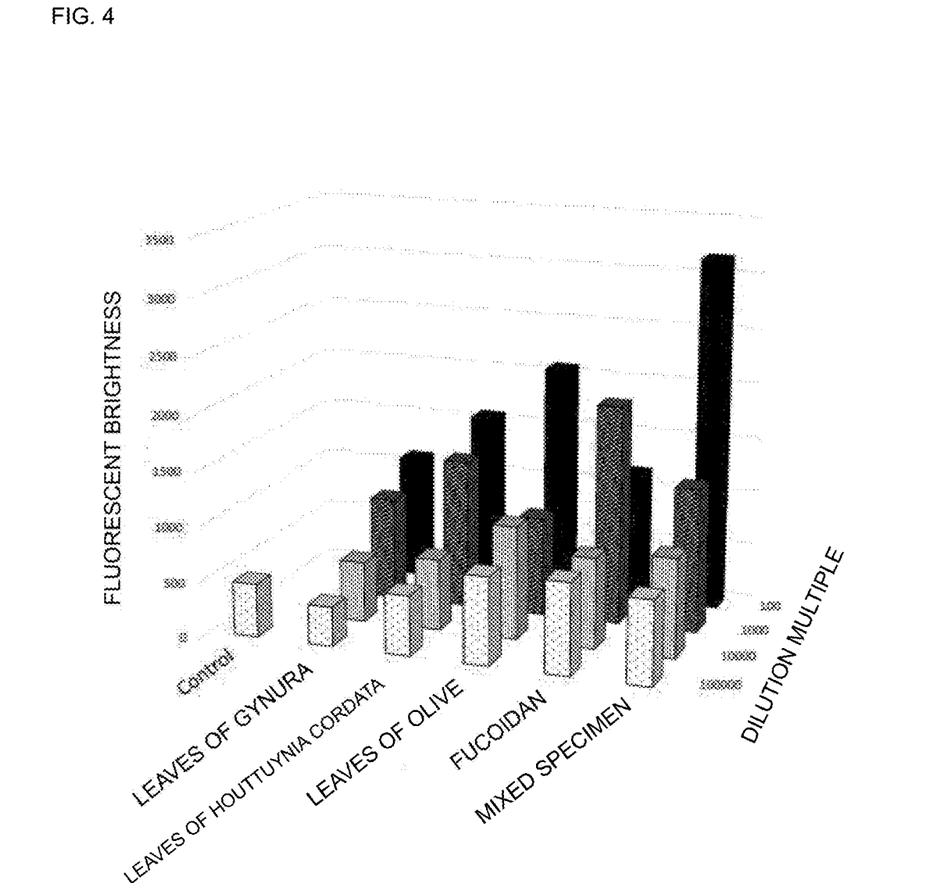
FIG. 4 illustrates a graph of results of a study of innate immune response.

As digitization, an image showing the state of uptake of fluorescent beads was obtained using a fluorescence microscope, and digitization processing was performed based on a total area of a certain fluorescent brightness or more in the image. The results are shown in FIG. 4. In FIG. 4, the amount of uptake fluorescence digitized for each added amount (dilution ratio) for each specimen was shown by a histogram.

Study of Acquired Immune Response

Mouse splenic lymphocytes (CD4+T cells) were isolated, and each specimen was diluted to 1/100, 1/1000 and 1/10000, respectively, added thereto, and then the mixture was cultured for 1 week. It shows that T cells differentiated into Th1 cells when the T cells produced IFN-γ, and differentiated into Th2 cells when the T cells produced IL-4, respectively.

Figure 5:
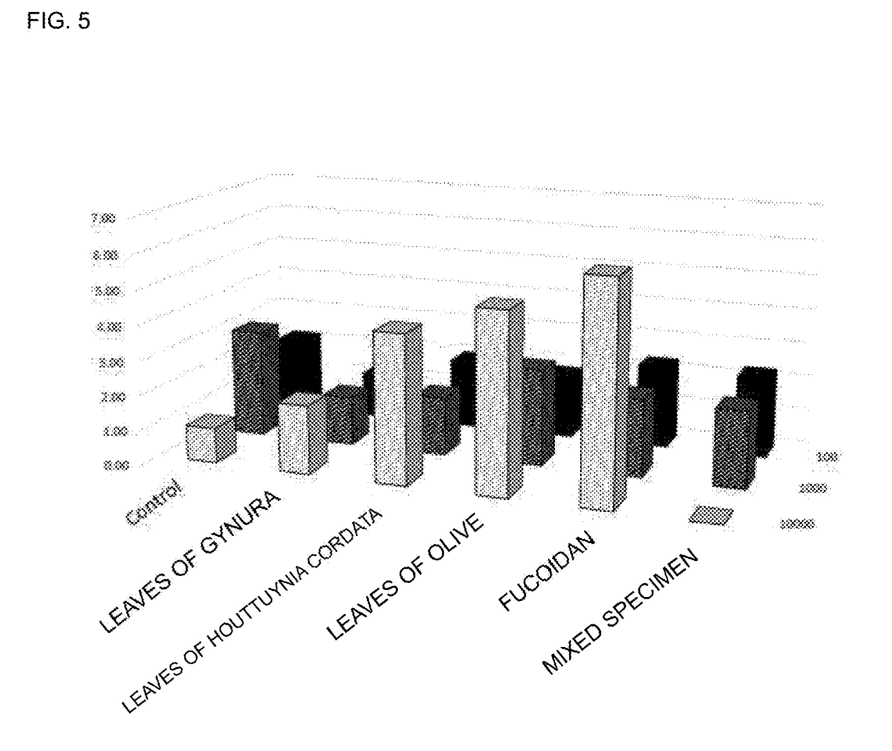
FIG. 5 illustrates a graph of results of a study of acquired immune response.

Therefore, after the culture, the lymphocytes producing IFN-γ were designated Th1 and the lymphocytes producing IL-4 were designated Th2, and the presence of each was measured using a fluorescently labeled antibody. For each specimen, the ratio of Th1/Th2 was determined for each dilution ratio from the measurement results. The results are shown in FIG. 5. For data of a dilution ratio of 10000 times of the mixed specimen of FIG. 5, Th1/Th2 was 94.5, but display was omitted from the viewpoint of easy viewing of FIG. 5.

From FIG. 4 and FIG. 5, it was revealed that the specimens of leaves of *Gynura* strongly influence the acquired immune response rather than the innate immune response. This suggests that an antitumor effect can be recognized when killer T cells, natural killer cells or the like are activated, or cell killing effect on tumor cells is recognized.

(3) Study of Cytotoxic Activity on Cancer Cells

Preparation of Specimens

The specimen A in the study of immune induction reaction was used as a specimen of leaves of *Gynura* used in the study of cytotoxic activity on cancer cells. (Hereinafter referred to as "specimen of leaves of *Gynura*" in this section)

Also, leaves of *Houttuynia cordata* and leaves of olive were used as specimens. A specimen was also prepared for fucoidan so as to have a concentration equivalent to the specimen of leaves of *Gynura*.

Study on Direct Cell Killing Effect on Cancer Cells

Figure 6:
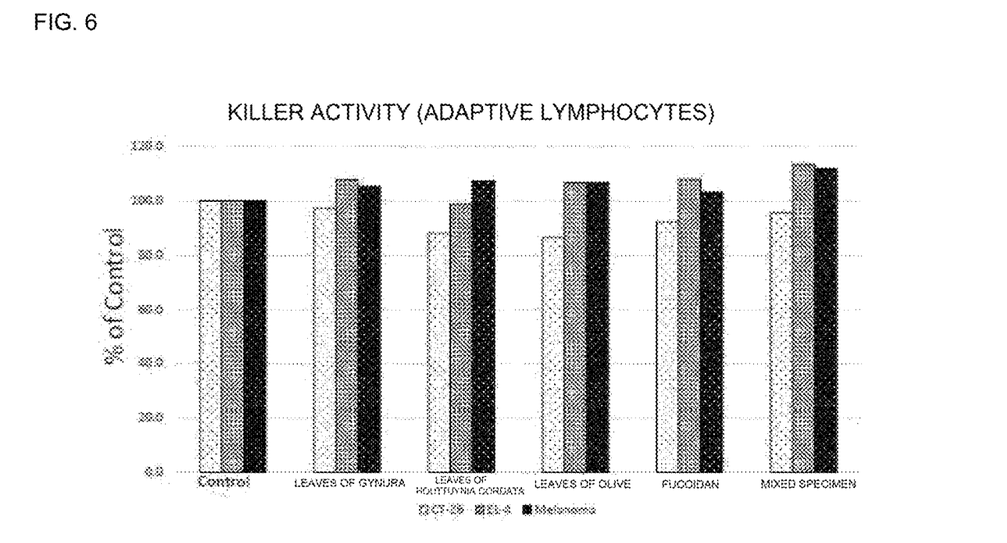
FIG. 6 illustrates a graph of results of a study of direct cell killing effect on cancer cells.

The cell killing effect of killing cells when culturing cancer cells and directly adding each specimen thereto was studied. Three types of cancer cells were studied, and representative mouse cancer cell lines of solid cancer, blood system cancer, and epidermal cancer were used (CT-26; colon cancer, EL-4; lymphoma, B16 mel; melanoma). As specimens, specimens of leaves of *Gynura*, leaves of *Houttuynia cordata*, leaves of olive and fucoidan, and a mixed specimen of the four kinds were used. The results are shown in FIG. 6.

All specimens showed no effect on EL-4 and B16 mel, but some effect was observed on CT-26. The effect was particularly strong in the specimens of leaves of olive and leaves of *Houttuynia cordata*.

Study of Cancer Cell Cytotoxic Activity Through Activation of Killer Cells and Natural Killer Cells Various specimens were added to lymphocytes isolated from mouse spleen and cultured for 1 week. Thereafter, culture was continued together with the cultured lymphocytes of the three types of separately cultured cancer cells. Here, when killer activity is induced, the lymphocytes injure cancer cells. For measuring this, measurement was performed using a cytotoxic activity assay kit (LDH Cytoxicity Detection Kit manufactured by Takara Bio Inc.).

As specimens, specimens of leaves of *Gynura*, leaves of *Houttuynia cordata*, leaves of olive and fucoidan, and a mixed specimen of the four kinds were used. In addition, Control was also used as a specimen. As cancer cells, CT-26, EL-4 and B16 mel were used.

In addition, lymphocytes were isolated from species adaptive and species maladaptive to the three types of cancer cells, respectively. Induction of cancer-specific killer activity can be considered that cancer cells are injured by adaptive lymphocytes and cancer cells are not injured by maladaptive lymphocytes. The results are shown in FIG. 7 as a ratio to Control.

Figure 7:
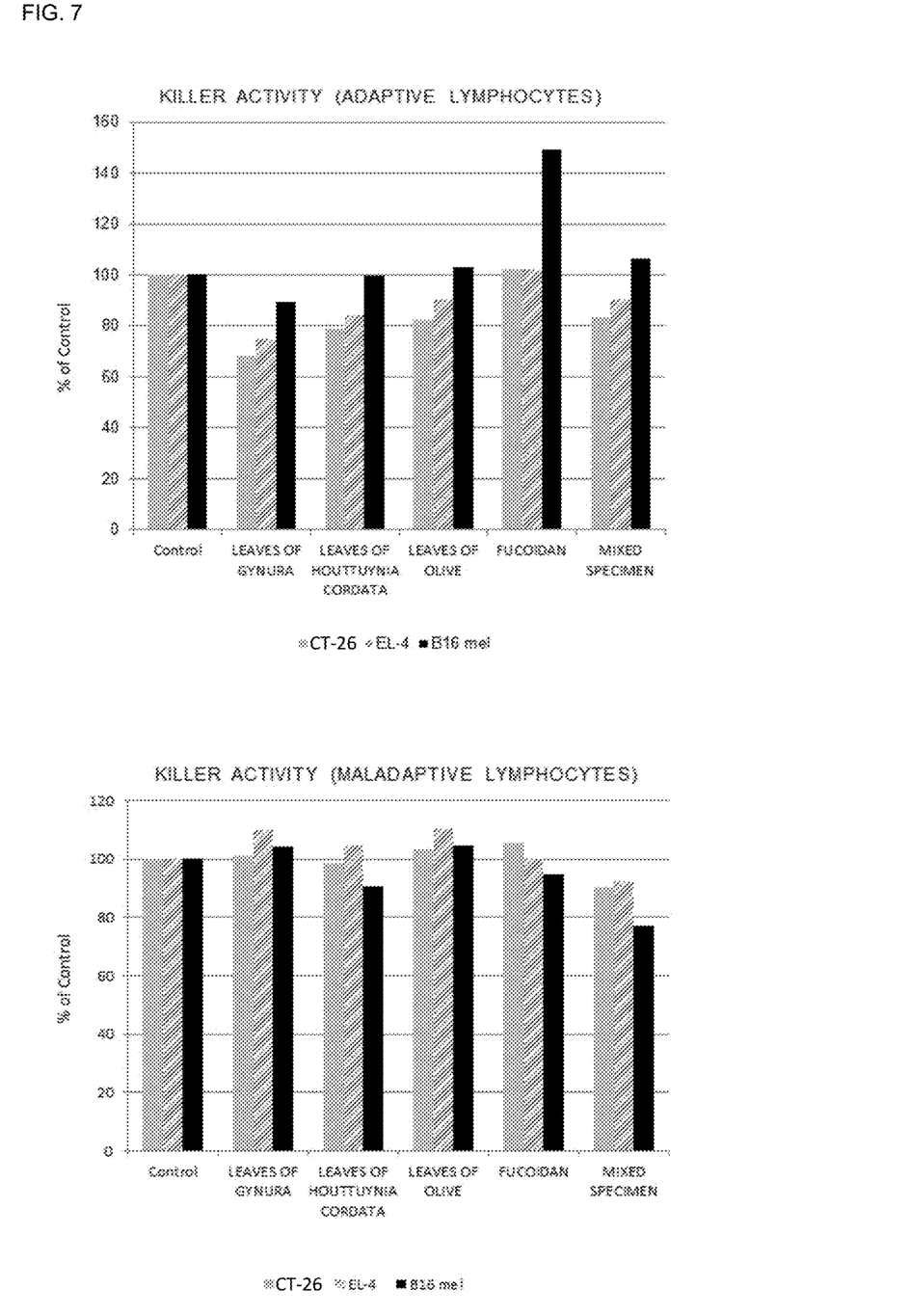
FIG. 7 illustrates graphs showing results of a study of cancer cell cytotoxic activity through activation of killer cells and natural killer cells.

As shown in FIG. 7, those in which the killer activity in the adaptive lymphocytes was recognized and the killer activity in the maladaptive lymphocytes was not recognized were the specimens of leaves of *Gynura*, leaves of *Houttuynia cordata* and leaves (fruits) of olive. Their actions were commonly strong against CT-26, and the effect was observed only in the specimen of leaves of *Gynura* in B16 mel. In addition, one having the strongest action on the whole was the specimen of leaves of *Gynura*.

In the mixed specimen of four kinds, fucoidan resulted in inhibiting the effect of other specimens.

The invention claimed is:
1. A method for producing an immune activator consisting essentially of:
   a drying step of low-temperature dehumidification drying *Gynura procumbens* at 0° C. or more and 40° C. or less and at 10% or less in relative humidity; and
   a cutting/pulverizing step of cutting or pulverizing the *Gynura procumbens* dried in the drying step while keeping at 0° C. or more and 40° C. or less.
2. The method for producing an immune activator according to claim 1, wherein at least one of leaves or stems of *Gynura procumbens* is used as the *Gynura procumbens*.
3. The method for producing an immune activator according to claim 1, further comprising a step of adding at least one of vitamins, olive or an extract of olive, and *Houttuynia cordata* or an extract of *Houttuynia cordata*.
4. A method for producing food and drink for immune activation, comprising a step of blending the immune activator obtained by the method for producing an immune activator according to claim 1, in a food or drink.
5. A medicine comprising the immune activator obtained from the method for producing an immune activator according to claim 1.
6. The method for producing an immune activator according to claim 1, wherein the low-temperature dehumidification drying is carried out by using a cooling type pulverizer.

* * * * *